United States Patent [19]

Goodchild et al.

[11] Patent Number: 4,806,463
[45] Date of Patent: Feb. 21, 1989

[54] INHIBITION OF HTLV-III BY EXOGENOUS OLIGONUCLEOTIDES

[75] Inventors: John Goodchild, Worcester; Paul C. Zamecnik, Shrewsbury, both of Mass.

[73] Assignee: Worcester Foundation for Experimental Biology, Shrewsbury, Mass.

[21] Appl. No.: 867,231
[22] Filed: May 23, 1986
[51] Int. Cl.$^4$ .................... C12Q 1/70; C12Q 1/02; A61K 39/12
[52] U.S. Cl. ............................ 435/5; 424/89; 435/6; 435/29; 435/32; 514/44; 536/26; 536/27; 536/28
[58] Field of Search ............ 435/5, 6, 29, 32; 424/9, 89; 536/26-28; 514/44

[56] References Cited

U.S. PATENT DOCUMENTS

| | | | |
|---|---|---|---|
| 4,469,863 | 9/1984 | Ts'o et al. | 536/27 |
| 4,511,713 | 4/1985 | Miller et al. | 536/27 |
| 4,587,044 | 5/1986 | Miller et al. | 530/211 |
| 4,665,032 | 5/1987 | Laurence | 435/948 X |
| 4,681,933 | 7/1987 | Chu et al. | 536/29 X |
| 4,689,320 | 8/1987 | Kaji | 514/44 |

OTHER PUBLICATIONS

Cianciolo et al., "Inhibition of Lymphocyte Proliferation by a Synthetic Peptide Homologous to Retroviral Envelope Proteins" Science 230, 453–455 (10/25/85).
Balzarini et al. "Comparative Inhibitory Effects of Suramin and Other Selected Compounds on the Infectivity and Replication of Human T–Cell Lymphotropic Virus (HTLV–III)/Lympadenophathy-Associated Virus (LAV)" Int. J. Cancer, 37, 451–457 (3/15/86).
Zamecnik et al. "Inhibition of Replication and Expression of Human T–Cell Lyphotropic Virus Type III in Cultured Cells by Exogenous Synthetic Oligonucleotides Complimentary to Viral RNA" Proc. Nat'l Acad. Sci. USA, 83, 4143–4146 (6/86).
Mitsuya et al. "Strategies for Antiviral Therapy in AIDS" Nature 325 773–778 (2/26/87).
Chandra et al. "Inhibitors of Retroviral DNA Polymerase: Their Implication in the Treatment of AIDS" Cancer Res. 45 4677s–4684s (9/85).
Balzarini et al., "Potent and Selective Anti-HTLV–III/LAV Activity of 2′, 3′-Dideoxycytidinene, the 2′,3′-Unsaturated Derivative of 2′,3′-Dideoxycitidine" Biochem Biophys Res Comm. 140, 735–742 (10/30/86).
Harper, M. E. et al., *Proceedings of the National Academy of Sciences, USA*, 83:772–776 (1986).
M. L. Stephenson and P. C. Zamecnik, *Proceedings of the National Academy of Sciences, U.S.A.*, 75:285–288 (1978).
P. S. Sarin et al., *Biochemical Pharmacology*, 34:4075–4079 (1985).
J. J. Toulme et al., *Proceedings of the National Academy of Sciences, U.S.A.*, 83:1227–1231 (1986).
P. F. Torrence et al., *Targets for the Design of Antiviral Agents*, E. DeClercq and R. Walker (ed.), pp. 259–285, Plenum Press (1984).
C. C. Smith et al., *Proceedings of the National Academy of Sciences, U.S.A.* 83:2787–2791 (1986).
P. S. Miller et al., *Nucleic Acids: The Vectors of Life*, pp. 521–535, D. Reidel Publishing Co. (1983).
E. S. Kawasaki, *Nucleic Acids Research*, 13(13):4991–5004 (1985).
K. R. Blake et al., *Biochemistry*, 24:6132–6138 (1985).
J. Goodchild et al., Abstract No. 1583, *Proceedings of the National Academy of Sciences, USA*, 45:1752 (1986).
P. Miller et al., *Federation Proceedings Abstract* 36,695, Abstract #2231 (1977).
P. J. Green et al., *Annual Review of Biochemistry*, 55:569–597 (1986).
K. R. Blake et al., *Biochemistry*, 24:6139–6145 (1985).
P. S. Miller et al., *Biochemistry*, 18:5134–5143 (1979).
P. S. Miller et al., *Journal of the American Chemical Society*, 93:6657–6665 (1971).
P. S. Miller et al., *Biochemistry*, 20:1874–1880 (1981).

Primary Examiner—Christine M. Nucker
Attorney, Agent, or Firm—Hamilton, Brook, Smith & Reynolds

[57] ABSTRACT

Inhibition of HTLV-III by adminstration of an oligonucleotide complementary to highly conserved regions of the HTLV-III genome necessary for HTLV-III replication and/or gene expression is described, as are oligodeoxynucleotide sequences which are complementary to those regions, methods of inhibiting HTLV-III replication and gene expression and methods of determining the presence or absence of HTLV-III virus in samples such as blood, saliva, urine and tears.

12 Claims, 1 Drawing Sheet

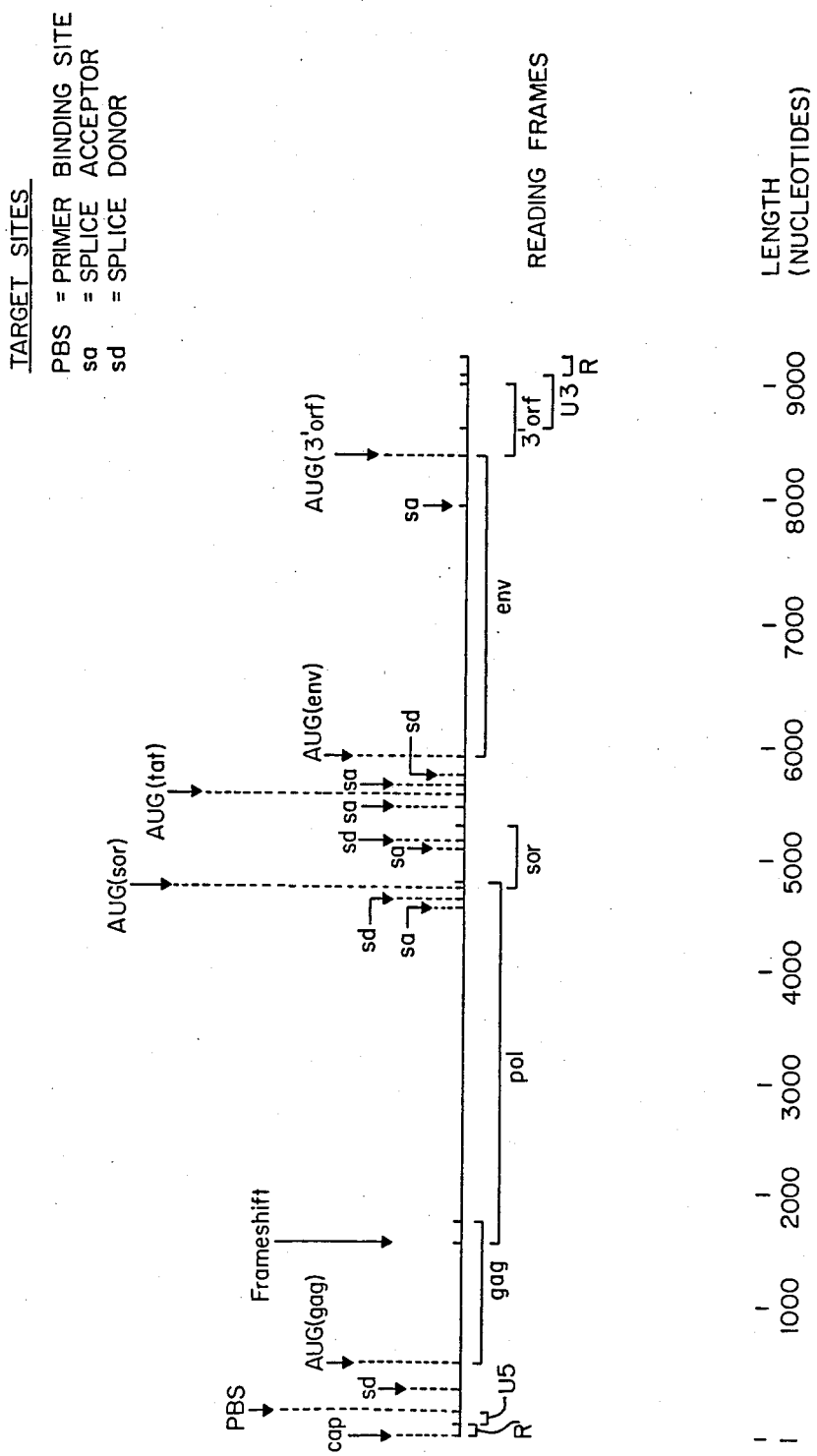

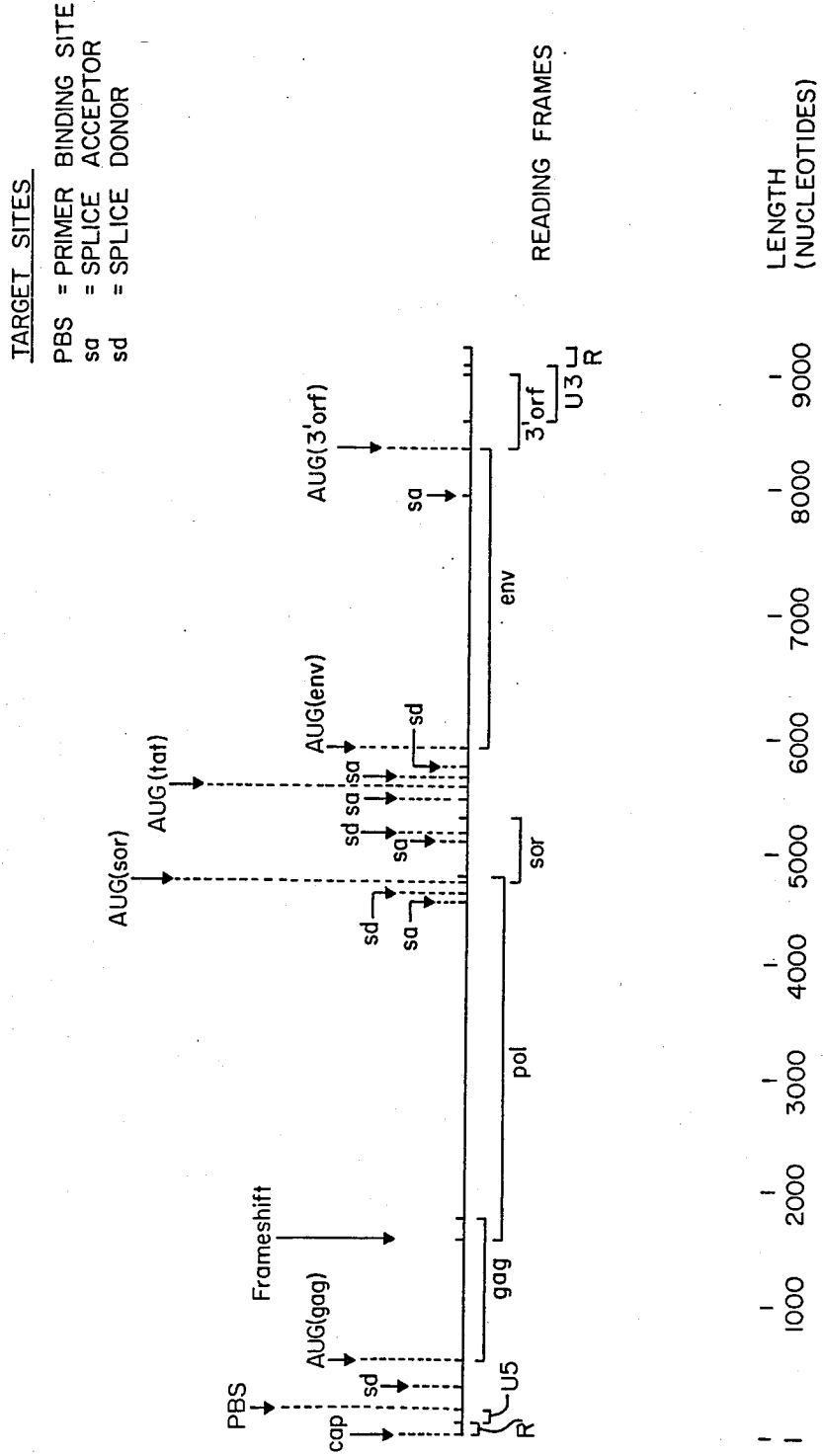

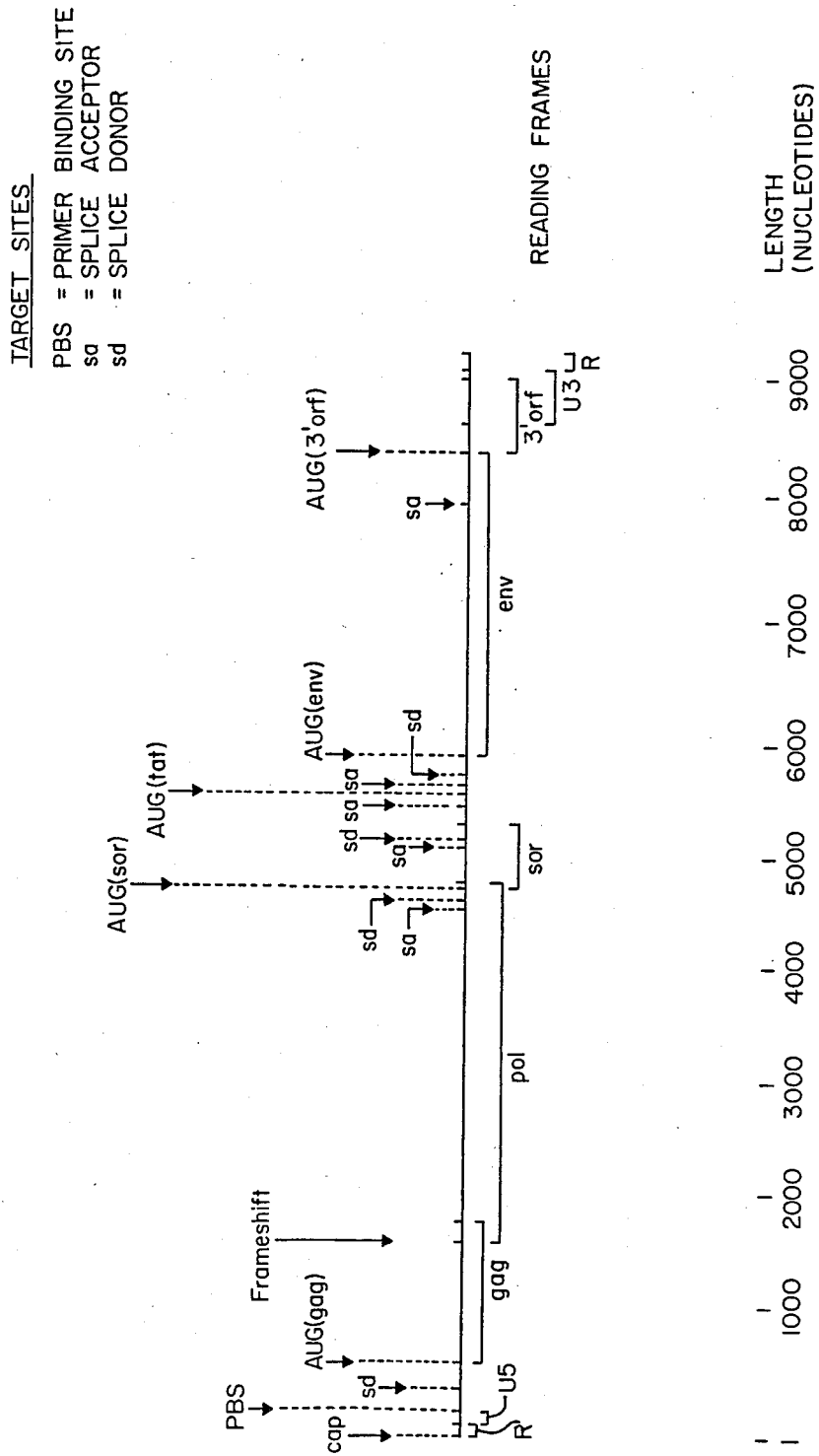

INHIBITION OF HTLV-III BY EXOGENOUS OLIGONUCLEOTIDES

BACKGROUND

Human T-cell leukemia-lymphotropic virus (HTLV) refers to a family of T cell tropic retroviruses. Such viruses, which have a role in causing certain T cell neoplasms, are presently divided into three main types or subgroups: (1) HTLV-type I (HTLV-I), which appears to cause adult T-cell leukemia-lymphoma (ATLL); (2) HTLV-type II (HTLV-II), which has been isolated from an individual having a T-cell variant of hairy cell leukemia; and (3) HTLV-type III (HTLV-III), which has been identified as the etiologic agent of acquired immune deficiency syndrome (AIDS). HTLV-III is also known as lymphadenopathy-associated virus (LAV), AIDS related virus (ARV) and human immunodeficiency virus (HIV). Popovic, M. et al., *Science,* 224: 497–500 (1984); Gallo, R. C. et al., *Science,* 224: 500–503 (1984); Wong-Staal, F. and Gallo, R. C., *Nature,* 317: 395–403 (1985); and Curran, J. W. et al., *Science,* 229: 1352–1357 (1985).

AIDS was first recognized in 1981 and since that time, the disease has come to be recognized as a new epidemic. *RNA Tumor Viruses* (2d edition), Volume 2, pp 437–443, Cold Spring Harbor Laboratory (1985).

Patients with AIDS exhibit clinical manifestations which include severe immunodeficiency which generally involves a depletion of helper T lymphocytes; malignancies; and opportunistic infections. The disease at this time is incurable and the mortality rate among AIDS patients is high.

Because the disease has severe, generally life threatening effects, there is great interest in finding means of protecting the population from it and of treating those who contract it. At the present time, much effort is being put into developing methods of detecting the presence of HTLV-III in body tissues and fluids (e.g., blood, saliva) and into developing vaccines which will protect recipients from HTLV-III. However, there is no known method which is satisfactory either for preventing the disease or for treating those who become infected with the virus. In fact, current efforts to develop a broad spectrum anti-HTLV-III vaccine may be seriously compromised, in light of the variation in envelope proteins (which are the principal antigenic determinants of the virus) observed among various strains of HTLV-III. Hahn, G. H. et al., *Proceedings of the National Academy of Sciences,* USA, 82: 4813–4817 (1985); Benn, S. et al., *Sciences,* 230: 949–951 (1985). Other methods of blocking the effects of the virus are clearly needed.

SUMMARY OF THE INVENTION

This invention relates to exogenous oligonucleotides which are complementary to regions of the HTLV-III genome and inhibit HTLV-III replication or gene expression; methods of inhibiting HTLV-III replication and HTLV-III gene expression in cultured human cells; methods of detecting the presence of HTLV-III in biological samples; and methods of administering the oligonucleotides to individuals for the purpose of inhibiting HTLV-III replication or gene expression.

The oligonucleotides of this invention, which can be oligodeoxyribonucleotides or oligoribonucleotides, are complementary to regions on the HTLV-III genome which are highly conserved, and whose function is necessary for normal replication or gene expression by HTLV-III. The oligonucleotides can be used to block HTLV-III replication, gene expression or both and thus can be used as chemotherapeutic agents in inhibiting replication and gene expression by the virus. In addition, they can be used to detect the presence of HTLV-III in samples such as blood, urine and saliva.

Oligonucleotides of the present invention are complementary to target sites which are highly conserved regions of the HTLV-III genome. These include the cap site; the primer binding site; nucleotide sequences vicinal to the primer binding site in the 5' direction; mRNA donor splice and acceptor splice sites; the HTLV-III initiator codons, including those for the *gag, sor,* the *tat,* the *env,* and the 3'ORF sequences; the *art* gene or a portion thereof; and the region of the genome responsible for the frameshift known to occur during transcription. These oligodeoxynucleotides can be used to inhibit HTLV-III replication and/or gene expression in the HTLV-III infected cells. They can be administered to individuals to block HTLV-III replication and/or gene expression as a means of chemotherapeutic treatment of acquired immune deficiency syndrome (AIDS) and of AIDS related complex (ARC).

Use of such oligonucleotides has at least two important advantages. First, the antiviral effects observed are very specific. For example, a specific sequence of 20 nucleotides would not be expected to occur at random more often than about one time in $10^{12}$. There are about $4 \times 10^9$ nucleotide pairs in the human genome and thus, the specificity of a 20-nucleotide sequence chosen from a conserved region of HTLV-III is predicted to be great. Second, the cellular toxicity of the oligonucleotides is also low, in comparison with most nucleoside analogues (e.g., those used in cancer chemotherapy, graft-host immunology and viral inhibition); such analogues are converted into nucleotides, which are subsequently incorporated into cellular DNA.

Oligonucleotides complementary to the same regions of the HTLV-III genome can be used to determine whether HTLV-III is present or absent in a sample such as blood, saliva or urine by determining whether cell death occurs in cells which are normally killed by HTLV-III virus (such as T lymphocytes) when they are cultured with the sample to be tested and whether cell death can be inhibited by the oligonucleotide.

BRIEF DESCRIPTION OF THE FIGURE

The FIGURE is a schematic representation of the primary nucleotide sequence of the HTLV-III genome and of the location on the genome of oligonucleotide competitive inhibition targets.

DETAILED DESCRIPTION OF THE INVENTION

The primary nucleotide sequence of the HTLV-III/-LAV genome has been determined by several groups of investigators. Ratner, L. et al., *Nature* 313: 277–284 (1985); Wain-Hobson, S. et al., *Cell* 40: 9–17 (1985); Sanchez-Pescador, R. et al., *Science* 227: 484–492 (1985); Muesing, M. A. et al., *Nature* 313: 450–458 (1985).

The genome of HTLV-III is shown in the FIGURE. The HTLV-III genome has been shown to be considerably more variable than the genomes of most retroviruses. *RNA Tumor Viruses* (2d edition) Volume 2, p 446, Cold Spring Harbor Laboratory (1985). Like other retroviruses, HTLV-III has in its genome three genes which encode viral proteins: (1) the *gag* gene, which encodes nucleocapsid or internal structural proteins of the virus; (2) the *pol* gene, which encodes reverse transcriptase (an RNA-directed DNA polymerase responsible for transcribing RNA into DNA); and (3) the *env* gene, which encodes the envelope glycoproteins of the virion. In addition, two other open reading frames are known; one (*sor*) overlaps with the 3' end of the *pol* gene and the other (3'ORF), located at the extreme 3' end of the genome, slightly overlaps the *env* gene and continues through most of the $U_3$ region. The genome has also been shown to contain tat-III and art. Tat-III is the trans-activation gene of HTLV-III; it gene encodes for trans-activator protein, which greatly accelerates viral protein synthesis in infected cells. Art (antirepression of the translation-transactivator gene) has only recently been found in the HTLV-III genome and appears to work cooperatively with tat in producing viral core and envelope proteins.

Other regions of the RNA of HTLV-III are a cap nucleotide, which occurs at the extreme 5' end of the genome; a short sequence (R) which is repeated at both ends of the RNA; a short sequence unique to the 5' end ($U_5$); and a sequence unique to the 3' end ($U_3$). Each of the last three components is present twice in viral DNA; each forms part of the long terminal repeat (LTR) sequence found at both ends of the unintegrated linear DNA product of reverse transcription. The HTLV-III genome also contains a primer binding site (PBS) adjacent to $U_5$ (at its 3' end); the PBS is complementary to the 3' end of tRNA lysine and functions as primer for synthesis of the minus strand of viral DNA. Donor splice (S.D.) and acceptor splice (S.A.) sites are also located on the viral RNA. Donor splice sites are sequences at which a 5' portion of the viral genome is joined to a portion of the 3' end of viral RNA, forming a spliced, subgenomic messenger RNA. Acceptor splice sites are sequences at which portions of the 3' end of viral RNA join donor splice sites to form subgenomic messenger RNA.

As mentioned above, different HTLV-III strains have been reported to have variations in envelope proteins. These variations may compromise the development of a broad spectrum anti-HTLV-III vaccine. In contrast, the primary nucleotide sequence of the primer area and certain other parts of the HTLV-III genome are highly conserved.

It has been now shown that complementary oligodeoxynucleotides directed toward such highly conserved regions of the HTLV-III genome inhibit virus replication and/or gene expression in cultured HTLV-III-transformed human lymphocytes.

TARGETED REGIONS OF THE HTLV-III GENOME

As mentioned, several regions of the HTLV-III genome are highly conserved; these regions or parts thereof can be targeted for inhibition by complementary oligonucleotide sequences. These regions, referred to as oligonucleotide competitive inhibition targets, include: (1) the cap site; (2) sequences of nucleotides 5' to the primer tRNA$^{lys}$ binding site; (3) the primer binding site or a segment thereof; (4) a combination of sequences 5' to the primer tRNA$^{lys}$ binding site and the primer binding site; (5) sequences of the mRNA donor or acceptor splice sites; (6) the initiator codons for the *gag*, the *sor*, the *tat*, the *env* and the 3'ORF sequences; (7) the *art* gene or portions thereof; and (8) the region of the genome responsible for the frameshift known to occur during transcription. The location of these regions (except the *art* gene) is indicated in the FIGURE; the *art* gene is located close to the *tat* gene.

It has been demonstrated that oligodeoxynucleotides complementary to four of the above mentioned highly conserved regions inhibit virus replication or gene expression in cultured HTLV-III-transformed human lymphocytes. That is, oligodeoxynucleotides complementary to (1) sequences 5' to the primary tRNA$^{lys}$ binding site; (2) the primer binding site; (3) sequences of a mRNA donor splice site; or (4) sequences of a mRNA acceptor splice site have been shown to cause inhibition. In general, any highly conserved region of the HTLV-III genome which encodes information necessary for viral replication or gene expression (e.g., protein synthesis) is a potential target for complementary oligodeoxynucleotides.

COMPLEMENTARY OLIGONUCLEOTIDE SEQUENCES

The oligonucleotide sequences complementary to the competitive inhibition targets can be oligoribonucleotide sequences or oligodeoxyribonucleotide sequences. Both types are referred to herein as oligonucleotides. As described here, the oligonucleotides were synthesized on an automated DNA synthesizer. It is possible, however, to produce the desired sequences by using genetically engineered organisms, such as bacteria or viruses.

Oligodeoxynucleotide sequences of varying lengths were used to assess their inhibitory effect on viral replication and gene expression. For example, several nucleotide sequences complementary either to nucleotide sequences of the HTLV-III genome which are 5' to the primer tRNA$^{lys}$ binding site or to nucleotide sequences which straddle the primer binding site and the adjacent region (in the 5' direction) were synthesized and their inhibitory effects tested. As described in greater detail in Example 3, a 12-nucleotide sequence (mer), a 20-nucleotide sequence and a 26-nucleotide sequence have been made and their inhibitory effects on viral replication and gene expression measured. The 12-nucleotide and the 20-nucleotide sequences are complementary to portions of the HTLV-III genome close to the primer binding site, in the 5' direction. The 26-nucleotide sequence is complementary to the primer binding site.

In addition, oligodeoxynucleotide sequences complementary to splice donor or splice acceptor sites of HTLV-III mRNA have been made and their inhibitory effects assessed. In particular, a 20-nucleotide sequence complementary to a splice donor site from the 3'-open reading frame region (FIG. 1) and two 20-nucleotide sequence complementary to the a-1 and a-1' splice acceptor sites, the former necessary for the production of transactivating factor, have been synthesized and their inhibitory effects measured.

Viral replication was assayed as reverse transcriptase activity level and gene expression as production of viral proteins p15 and p24. Inhibition of viral replication is reflected in reduced reverse transcriptase activity levels; inhibition of viral gene expression is indicated by reduction in viral protein production. As shown in Table 1, HTLV-III replication and protein expression were inhibited in almost every instance. The greatest inhibitory effect was evident when the 20-nucleotide sequence complementary to the splice acceptor site was tested on cultures of HTLV-III infected cells.

Other complementary oligonucleotide sequences which can be used are determined by the competitive inhibition target(s) selected. Oligonucleotide sequences can be complementary to a single competitive inhibition target or can be complementary to more than one such target. For example, sequences can be produced which are complementary to the HTLV-III primer binding site and the region of the genome immediately adjacent to that site in the 5' direction; to two splice donor sites; to two splice acceptor sites; or to any combination of competitive inhibition targets.

Other characteristics of the oligonucleotides used to inhibit viral processes include their length; their modification and the location of groups used to modify them. For example, the length of the oligonucleotides to be used will be determined by factors such as the desired specificity of inhibition, size necessary to block viral function, and effect on transmembrane passage. For example, the work described herein has made use of complementary oligodeoxynucleotides ranging in length from 14 to 26 nucleotides. However, there is potentially no limit to the length of the oligonucleotides to be used and length must be determined carefully, in light of the fact it plays a role in viral inhibition. Generally, oligonucleotides used to inhibit HTLV-III will be 8-50 nucleotides in length.

Oligonucleotides to be used can be modified at a variety of locations along their length. For example, they can be modified by the addition of groups at the 5' end, the 3' end or both, as well as on the internal phosphate groups or on the bases. Whether oligonucleotides to be used are modified and, if so, the location of the modification(s) will be determined, for example, by the desired effect on viral activity (e.g., inhibition of viral replication, gene expression or both), uptake into infected cells, inhibition of degradation of the oligonucleotides once they are inside cells, and prevention of their use as a primer by reverse transcriptase. For example, if inhibition of reverse transcriptase activity (and thus of viral replication) is desired, it may be necessary to block the 3' end of a sequence complementary to the primer binding site and/or sequences vicinal to the primer binding site in the 5' direction (for example by a 2'3' dideoxynucleotide). In this way, the oligonucleotide complementary to either or both of those regions cannot itself serve as a template for transcriptase activity. If the desired effect is increased uptake of the oligonucleotide into infected cells, modification of the oligonucleotide by addition of a lipophillic group at the 5' end would be beneficial. Modification of oligonucleotides can also be carried out by the addition of an intercalating agent (e.g., acridine dye) at 5' or 3' termini, on bases, or on internucleophosphate groups. Modification in this manner may result in stronger binding between the oligonucleotides and the HTLV-III nucleic acids. Asseline, U. et al., *C.R. Acad. Sc. Paris*, 369-372 (1983). As shown in Table 1, the 12 nucleotide sequences complementary to the region of the HTLV-III genome 5' to the primer binding site were blocked at the 3' end by ddT. Early work on Rous sarcoma virus inhibition indicates that the 3' end blocked hybridon was a more effective inhibitor than an unblocked hybridon. A hybridon is defined as an oligonucleotide complementary to single-stranded DNA or RNA, which modulates the function of the DNA or RNA by competitive hybridization. Zamecnik, P. and M. L. Stephenson, *Proceedings of the National Academy of Sciences, USA*, 75: 280284 (1978).

Chain terminator(s) to be used in modifying oligonucleotides for use in inhibiting viral replication and gene expression can be, for example, ddT (as described above and in Example 3), the isourea group, the dimethoxytrityl group, or, in fact, any 3' modified function. Selection of the chain terminator is based, for example, on the absence of a 3' OH group (which can act as a substrate for reverse transcriptase); lack of or low cellular toxicity; lipophilicity; and lack of impairment of hydrogen bonding properties of the oligonucleotide.

INHIBITION OF HTLV-III-INFECTED CELLS

Using the oligodeoxynucleotide sequences described above and in Example 3, it was possible to inhibit HTLV-III replication and gene expression in HTLV-III-infected cells in tissue culture. The oligodeoxynucleotides described were added to peripheral human blood cells (PB) infected with HTLV-III and to transformed T-lymphocyte (H9) cells infected with HTLV-III. The oligodeoxynucleotide was usually added at time zero only and observation of inhibitory effects was made at 96 hours. In one case, the oligonucleotide was added to fresh culture medium daily for 3 days. Reverse transcriptase activity and viral p15 and p24 protein production were used as indicators of inhibition of HTLV-III replication and gene expression, respectively. As shown in Table 1 and described in detail in Example 3, inhibition was greatest when a 20-nucleotide sequence complementary to a splice acceptor site was added to HTLV-III-infected transformed T-lymphocytes. Inhibition was observed under essentially all experimental conditions (see Table 1).

Important considerations in this context are the concentration at which the complementary oligodeoxynucleotides are applied and the timing (scheduling) of their administration. As shown in Table 1, the oligodeoxynucleotides were added at concentrations ranging from 5 μg/ml. to 50 μg/ml. culture medium. These concentrations were generally effective in producing an inhibitory effect but this range is by no means to be considered limiting. As described, the oligodeoxynucleotide was usually added at one time only; it seems, however, that daily addition (or more frequent addition) is more effective than a single dose.

INHIBITION OF HTLV-III IN HUMANS

Based on the information gained from inhibition of HTLV-III-infected cells in tissue culture, it is possible to formulate a strategy for similar inhibition of HTLV-III in AIDS patients, as well as in individuals carrying the AIDS virus but not manifesting symptoms of the disease.

The strategy used in treating a particular individual depends on the status of the individual and the objective of the treatment. That is, an individual who has been found to be carrying the HTLV-III virus but shows no symptoms of AIDS might be treated differently, in terms of both the type of oligonucleotide(s) administered and the dose given, than an individual who does, in fact, have AIDS. In addition, treatment might well differ if its objective is to protect uninfected cells or to have an effect on cells which are already infected.

For example, an individual known to be harboring the virus but yet manifesting no sign of AIDS could be given a long-term or lifetime maintenance dose of oligonucleotides whose inhibitory effects stop reverse transcription (e.g., oligonucleotides complementary to the primer binding site and/or sequences close to the primer binding site in the 5' direction). In this way, the first step in viral life or replication is inhibited because viral DNA cannot be made and the virus is unable to proliferate. However, in an AIDS patient, cells are already infected and treatment must inhibit expression of genes (viral DNA) already present in the infected cells. In this case, oligonucleotides complementary to, for example, initiator codons for genes encoding viral proteins, are required to prevent viral construction. In an AIDS patient, uninfected cells can also be protected by administration of oligonucleotides capable of blocking reverse transcription.

In any treatment situation, however, oligonucleotides must be administered to individuals in a manner capable of getting the oligonucleotides initially into the blood stream and subsequently into cells. As a result, the oligonucleotides can have the desired effects: getting into HTLV-III infected cells to slow down or prevent viral replication and/or into as yet uninfected cells to provide protection.

Oligonucleotides whose presence in cells can stop reverse transcription and oligonucleotides whose presence in cells can inhibit protein synthesis can be administered by intravenous injection, intravenous drip or orally. The dose to be administered varies with such factors as the size and age of the patient, stage of the disease and the type of oligonucleotide to be given.

DETECTION OF THE HTLV-III VIRUS IN SAMPLES

The oligonucleotide sequences of the present invention can also be used in determining whether the HTLV-III virus is present or absent in samples such as blood, urine, saliva and tears. An aliquot of the sample to be analyzed is added to a culture of cells which are normally killed by the HTLV-III virus (e.g., T lymphocytes); this is the control. A second aliquot is added to a separate culture of T lymphocytes, along with oligonucleotides complementary to one or more of the regions of the HTLV-III genome describe above; this is the test sample. Both cultures are maintained under conditions appropriate for growth and subsequently analyzed (e.g., visually/microscopically) for growth of the T lymphocytes. If the HTLV-III virus is present, the T lymphocytes in the control sample will be killed; if not, the T lymphocytes survive. T lymphocytes in the test sample, however, will continue to be viable because of the protection provided by the complementary oligonucleotides included in the culture. Visual comparison of the two samples makes it possible to determine whether HTLV-III virus is present or absent in each.

The present invention will now be further illustrated by the following examples, which are not intended to be limiting in any way.

EXAMPLE 1

Synthesis and Characterization of Oligodeoxynucleotides

Unmodified oligodeoxynucleotides were synthesized on an automated DNA synthesizer (Biosearch SAM I), using either standard triester or phosphoramidite chemistry. Gait, M. J. (Ed.), *Oligonucleotide Synthesis*, I.R.L. Press (1984). After deblocking, the products were purified first on Merck silica gel 60 thin layer chromatographic plates in i-propanol: concentrated ammonia:water (55:35:10) and eluted with ethanol:water (1:3). Where necessary, further purification was performed by high pressure liquid chromatography, using a Waters SAX Radial-Pak catridge or by polyacrylamide gel electrophoresis (PAGE). The synthetic, preparative and analytical procedures have been described in detail. See Gait, M. J., above. The oligonucleotide with terminal 3'-deoxythymidine (ddT) was made by the solution phase triester method. This method is described in detail by Narang, S. A. et al., in: *Methods in Enzymology*, L. Grossman and K. Moldave (Ed.), 65: 610–620, Academic Press (1980), the teachings of which are incorporated herein by reference. ddT (Sigma) was used directly in the coupling reaction without protecting groups. The final product was purified first on 2 mm thick silica gel plates (Analtech) as above and subsequently by column chromatography on DEAE cellulose in a gradient of 0.02–0.8M triethylammonium bicarbonate.

Oligonucleotides were 5'-end-labeled by T4 polynucleotide kinase, purified by polyacrylamide gel electrophoresis (PAGE) and sequenced by either the Maxam-Gilbert or wandering spot methods. Maxam, A. M. and W. Gilbert, in: *Methods in Enzymology*, L. Grossman and K. Moldave (ed.) pp 499–560, Academic Press (1980); Jay, E. et al., *Nucleic Acids Research*, 1: 331–353 (1974). For Maxam-Gilbert sequencing of fragments of this size, it was found necessary to increase reaction times up to 30 minutes at 37°. The presence of ddT at the 3' end of oligodeoxynucleotide did not seem to hinder the action of the exonuclease snake venom phosphodiesterase.

EXAMPLE 2

Oligodeoxynucleotide uptake studies

HeLa cells were grown in suspension culture, concentrated by centrifugation at 600×g for 5 min. and resuspended at a concentration of $5 \times 10^7$ to $5 \times 10^8$ cells/ml of Dulbecco's modified Eagle's medium (DME) without serum and kept on ice. Synthetic oligodeoxynucleotides to be tested (10-30 nucleotides in length), were labeled with $^{32}P$ at the 5'-end by polynucleotide kinase at $2 \times 10^5$ cpm/nmol, dissolved in DME without serum, and added to the HeLa cell suspension (40 μl oligodeoxynucleotide solution to 0.7 ml ice cold HeLa cell suspension.). Alternatively, to generate an internally labelled oligonucleotide, two decamers, one of them 5'$^{32}P$ labelled, were joined by T4 DNA ligase in the presence of an oligodeoxynucleotide (12 nucleotides long) part of which was complementary to the 5' end of one of the decamers and part of which was complementary to the 3' end of the other decamer. The concentration of labelled oligodeoxynucleotide in the HeLa cell suspension was usually $1 \times 10^{-5}$ to $1 \times 10^{-7}M$. Cells were incubated under sterile conditions at 37° for up to 20 hours. Samples were cooled at 0°, diluted to 10 ml with DME, and centrifuged lightly to pellet the cells. The supernatant fluid was poured off and saved and the centrifugation tube drained on filter paper. The cell pellets were then washed six times, each time in 9 ml of ice-cold DME. The supernatants were saved and monitored for $^{32}P$ radioactivity. By the sixth wash, virtually no radioactivity was detected in the wash fluid. The cell pellets were then resuspended on 0.7 ml of ice cold DME and transferred to an electroporation cell. Electroporation was carried out at 0° by a variation of the technique described by Potter and co-workers in Potter et al., *Proceedings of the National Academy of Sciences, USA*, 81: 7161–7165 (1984), the teachings of which are incorporated herein by reference. During electroporation, a short high voltage pulse was applied across the electroporation cuvette containing the cell pellets; in this way, the cell membranes were made temporarily leaky or porous, allowing oligonucleotides to pass out of the cells. The electroporation cuvette was kept in an ice bath for 15 min. following electroporation. The contents were transferred to a 1.5 ml Eppendorf microfuge tube, and centrifuged 5 min. at 12,000×g. The supernatant solution (i.e., oligomer which has entered the cell) was removed, and radioactivity of both the supernatant and the pellet (which contained the nuclear and cell membrane component) was determined by scintillation counting.

Two other variants of this method were also used to determine whether externally added labeled oligodeoxynucleotides enter CEF and HeLa cells. In the case of CEF cells, which had been grown in monolayers in 75 cm² Falcon flasks, the DME medium containing serum was removed, the cells were washed once with serum-lacking DME; 2 ml of DME containing $^{32}$P-labeled oligodeoxynucleotide were added; and the resulting combination was incubated at 37° C. for 15 minutes. The cells were next washed six times at 37° C. (ambient), each time with 10 ml of DME. 2 ml of 1N formic acid was then added, and the cells were kept on ice for 15 min. The same procedure was carried out with CEF or HeLa cells except that instead of 1N formic acid, distilled water was added after incubation to lyse the cells. Results were similar with both procedures; approximately half as much radioactivity was associated with the nuclear and cell membrane fraction (sedimented by centrifugation 5 min. at 12,000×g) as was associated with the non-sedementing fraction of the cell.

The possibility that treatment of labeled cells with either 1N formic acid or distilled water caused dissociation of radiolabeled oligomer (which had never entered the interior of the cell) from the cell membrane fraction was tested by using the above modified electroporation technique as described. Results using electroporation agree with those where cells were ruptured by hypotonicity or 1N formic acid.

These tests made it possible to assess uptake of $^{32}$P-oligonucleotides by the cultured cells described. Inhibition of viral replication by exogenous oligodeoxynucleotides depends upon their uptake in sufficient amounts by the cells; this is not the case when endogenously transcribed or microinjected anti-sense RNAs are used. The permeability of cultured mammalian cells to the oligodeoxynucleotides has been demonstrated by these tests to be as follows:

(1) Under the experimental methods described, cellular uptake of 20-nucleotide sequences, labeled with $^{32}$P either internally or terminally, increased during the initial few hours of incubation. At an external concentration of $1\times10^{-7}$M, after 4 hours of incubation at 37° C., the internally labeled 20 -nucleotide sequence TAGTCTCAAT-$^{32}$P-GGGCTGATAA reached a concentration inside the HeLa cell of approximately $2\times10^{-9}$M. In another experiment conducted using the same conditions described, at an external concentration of $2\times10^{-5}$M, after 15 minutes of incubation at 37° C., the internally labelled 20-nucleotide sequence TAGTCTCAAT-$^{32}$P-GGGCTGATAA reached an apparent concentration inside the CEF cell of about $1.5\times10^{-6}$M.

(2) At 15 min. and 4 hour time periods labeled oligodeoxynucleotides released from the cells by electroporation were largely intact, as judged both by migration on thin layer DEAE plates, in Homo V Jay, E. et al., *Nucleic Acids Research,* 1: 331-353 (1974), and by PAGE using oligodeoxynucleotide markers. However, degradation of oligodeoxynucleotides increased with incubation time. By 20 hours, a large fraction of oligodeoxynucleotide was degraded intracellularly and extracellularly, but undergraded oligomer was still detected, and thus endured long enough to have the desired inhibiting effect.

(3) Terminally labeled oligodeoxynucleotides disappeared more rapidly than those labeled internally. This indicates that *phosphomonoesterase* activity is more rapid than *endonuclease* activity.

EXAMPLE 3

Inhibition of HTLV-III replication by complementary oligodeoxynucleotides

The primary nucleotide sequence of the HTLV-III/-LAV genome has been determined during the past year by several groups of investigators, as indicated above. The following regions of the genome were selected as oligonucleotide competitive inhibition targets: (a) a sequence of nucleotides 5' to the primer tRNA$^{lys}$ binding (association) site; (b) a sequence straddling the primer binding site and the adjacent region, in the 5' direction; (c) a sequence at the primer binding site and (d) sequences from the splice sites (i.e., splice donor site, splice acceptor site) of the pre-mRNA that expresses the 3'-open reading frame regions. Sodroski, J. et al., *Journal of Virology,* 55: 831–835 (1985); Wong-Staal, F. and Gallo, R. C., *Nature,* 317: 395–403 (1985). Their locations on the HTLV-III/LAV genome are indicated in FIG. 1.

(A) Sequences complementary to the primer binding site and sequences vicinal to the primer binding site in a 5' direction.

Several sequences complementary to regions immediately adjacent, in a 5'-direction, to the tRNA$^{lys}$ primer binding site in HTLV-III, or complementary to the primer binding site were synthesized. These are a 12-nucleotide sequence (5'CTGCTAGAGATddT) a 20-nucleotide sequence (5'-CTGCTAGAGATTTT-CCACAC), and a 26-nucleotide sequence with a 3' terminal non-complementary tail of (pA)$_3$ (5'-TTCAAGTCCCTGTTCGGGCGCCAAAA). As shown in Table 1, the 12-nucleotide sequence is complementary to a sequence of nucleotides close to the primer binding site (in the 5' direction); the 20-nucleotide sequence is also complementary to a sequence close to the primer binding site in the 5' direction, and includes the first 11 nucleotides of the 12-nucleotide sequence, as well as nine additional nucleotides. The 26-nucleotide sequence is complementary to the primer binding site. These oligodeoxynucleotides were tested on tissue cultures of HTLV-III-infected cells; they were added to the cultures at the concentrations shown in Table 1 (column 3). Both reverse transcriptase activity and production of viral-encoded p15 and p24 proteins were measured to determine inhibition of viral replication and inhibition of gene expression, respectively.

TABLE I

Inhibition of HTLV-III Replication and Protein Expression by Complementary Oligodeoxynucleotides

| Sequence | Oligomer Length | Conc. μg/ml | HTLV-III Binding Site | Cell Line | HTLV-III Added | Percent Inhibition RT | p15 | p24 |
|---|---|---|---|---|---|---|---|---|
| 0 | | | | H9 | − | 0 | 0 | 0 |
| 0 | | | | H9 | + | 0 | 0 | 0 |
| CCCCAACTGTGTACT | 15 | 5 | none | H9 | + | 0 | 0 | 0 |
| " | " | 10 | none | H9 | + | 0 | 0 | 0 |
| CTGCTAGAGATddT | 12 | 5 | 5'-vicinal to PBS | PB | + | 30 | 0 | 17 |
| " | " | 10 | " | " | + | 36 | 0 | 50 |
| " | " | 20 | " | " | + | 40 | 35 | 36 |
| " | " | 5 | " | H9 | + | 10 | 15 | 35 |
| " | " | 10 | " | " | + | 17 | 15 | 50 |
| " | " | 10 | " | H9 | + | 0 | 10 | 12 |
| " | " | 20 | " | " | + | 0 | 28 | 38 |
| CTGCTAGAGATTTTCCACAC | 20 | 50 | " | PB | + | 50 | 50 | 50 |
| " | " | 10 × 3+ | " | H9 | + | 50 | 75 | 75 |
| " | " | 50 | " | " | + | 23 | 27 | 30 |
| TTCAAGTCCCTGTTCGGGCGCCAAAA | 26 | 50 | at PBS≠ | H9 | + | 80 | 4 | 8 |
| GCGTACTCACCAGTCGCCGC | 20 | 50 | splice donor site | H9 | + | 85 | 40 | 60 |
| CTGCTAGAGATTAA | 14 | 50 | 5'-vincinal to PBS§ | H9 | + | 75 | 8 | 11 |
| ACACCCAATTCTGAAAATGG | 20 | 50 | splice acceptor site | H9 | + | 67 | 95 | 88 |

+10 ug/ml. on days 1,2 and 3 from time of infection
≠Has 3 non-complementary bases at 3' end
§Has 2 non-complementary bases at 3' end
A+ PBS indicates directly competing at primer binding site
PB: peripheral human blood cells
H9: transformed immortalized human T cell line Reverse transcriptase activity was measured by the method described by Sarin and co-workers, which is a modification of an earlier method described by Baltimore and Smoller. The modified method is described in Sarin, P. S. et al., *Biochemica Biophysica Acta*, 470: 198–206 (1977) and the earlier method in Baltimore, D. and Smoller, D., *Proceedings of the National Academy of Sciences, U.S.A.*, 68: 1507–1511 (1971); the teachings of both references are incorporated herein by reference.

HTLV-III-protein expression was measured by immunofluorescence using monoclonal antibodies to HTLV-III p15 and p24 as described in Sarin et al., *Biochemistry and Pharmacology*, 34: 4075–4078 (1985), the teachings of which are incorporated herein by reference.

In separate experiments, peripheral human blood cells and transformed T-lymphocyte (H9) cells were infected with HTLV-III; the oligodeoxynucleotides were added just once (at time zero), unless otherwise indicated. Assays for inhibition were carried out at 96 hours.

(B) Sequences complementary to splice sites of pre-mRNA

A 20-nucleotide sequence complementary to a splice donor site from the 3'-open reading frame region, and a 20-nucleotide sequence complementary to a splice acceptor site were produced. These oligodeoxynucleotides were tested as described in part A (above); their effects were also measured through determintion of reverse transcriptase activity and production of viral-encoded proteins.

(C) Results of inhibition tests

The results of testing using the oligodeoxynucleotides described in (A) and (B) of this example are shown in Table 1. The greatest inhibition occurred when an oligonucleotide having the sequence ACACCCAATTCTGAAAATGG, which is complementary to the splice acceptor site in H9 cells, was added at 50 μg/ml ($9 \times 10^{-6}$M). Percent inhibition as shown in the table is based on comparison with control values obtained for HTLV-III-infected cells incubated without oligodeoxynucleotide. As indicated in Table 1 (columns 7-9), reverse transcriptase activity was inhibited by 67%, p15 protein production by 95% and p27 protein production by 88% when this sequence was used. The oligodeoxynucleotide was given just once (at time zero), and inhibitory effects were observed at 96 hours. Marked inhibition was also found with the other oligodeoxynucleotides, as shown in Table 1.

For example, when the 12-mer sequence complementary to the region of the HTLV-III/LAV genome adjacent, in the 5' direction, the tRNA$^{lys}$ primer binding site was added to HTLV-III-infected cells at the concentrations shown in Table 1, reverse transcriptase activity was inhibited from 10–17% in H9 cells and 30–40% in PB cells. Viral p15 and p24 protein production was inhibited by 15% and by 35–50%, respectively, in H9 cells; in PB cells, inhibition of p15 protein production ranged from 0–35% and of p24 protein production, from 17–50%. When the 20-nucleotide sequence was used, reverse transcriptase activity was inhibited in H9 cells by 23–50% and viral protein production by 27–75%. Fifty percent inhibition of all three activities was observed in PB cells as a result of addition of the 20-nucleotide sequence. Based on work on inhibition of Rous sarcoma virus in tissue culture, it seems likely that daily addition of competitor oligodeoxynucleotide is more effective than a single dose at time zero. Zamecnik, P. C. and M. L. Stephenson, *Proceedings of the National Academy of Sciences, USA*, 75: 280–284 (1978). This is also consistent with time-related intracellular and extracellular degradation of added oligodeoxynucleotide, since measurement of efficacy occurs at 96 hours. Although overall variation in assays of other chemotherapeutic agents for HTLV-III is in the vicinity of ±5 percent, it is considerably higher where oligodeoxynucleotides are being tested (cf. Table I). This may be related to variable nuclease activity, both intracellular and extracellular, in tissue cultures of H9 and PBS cells. Such an effect would be more marked at lower concentration of oligodeoxynucleotides. Oligodeoxynucleotides blocked at the 3' end by ddT, the isourea group, or other chain terminators may prove to be more effective inhibitors than those described above. For example, work on inhibition of Rous sarcoma virus has shown that the 3' end blocked hybridon was a more effective inhibitor than a hybridon having an unblocked 3' end. This is particularly pertinent to prevention of initiation of replication at loci close to the primer binding site.

We claim:

1. A therapeutic composition comprising an oligonucleotide capable of hybridizing with a highly conserved region of the HTLV-III genome, and a physiologically acceptable carrier, the oligonucleotide consisting essentially of a nucleotide sequence which is complementary to a region of the HTLV-III genome selected from the group consisting of:
  (a) the tRNA$^{lys}$ primer binding site;
  (b) regions of the HTLV-III genome vicinal in the 5' direction to the tRNA$^{lys}$ primer binding site;
  (c) the tRNA$^{lys}$ primer binding site and regions of the HTLV-III genome vicinal in the 5' direction to the tRNA$^{lys}$ primer binding site;
  (d) the mRNA donor splice sites;
  (e) the mRNA acceptor splice sites;
  (f) the initiator codon for the gag gene;
  (g) the initiator codon for the env gene;
  (h) the initiator codon for the tat gene;
  (i) the initiator codon for the sor gene;
  (j) the initiator codon for the 3' orf gene;
  (k) the cap nucleotide of the HTLV-III genome;
  (l) the art gene or portions thereof;
  (m) the region of the HTLV-III genome encoding a frameshift; and
  (n) equivalents thereof, said equivalents being nucleotide sequences which are sufficiently similar in sequence to the complementary nucleotide sequences to be capable of hybridizing with a conserved region of the HTLV-III genome and inhibiting its activity.

2. An oligodeoxynucleotide of claim 1 which is at least 8 nucleotides long.

3. An oligodeoxynucleotide of claim 2, said oligodeoxynucleotide being selected from the group consisting of:
  (a) CTGCTAGAGATddT;
  (b) CTGCTAGAGATTTTCCACAC;
  (c) TTCAAGTCCCTGTTCGGGCGCCAAA;
  (d) GCGTACTCACCAGTCGCCGC;
  (e) CTGCTAGAGATTAA;
  (f) ACACCCAATTCTGAAAATGG; and
  (g) equivalents thereof.

4. A method of inhibiting HTLV-III replication, HTLV-III gene expression or both in cells containing HTLV-III, comprising contacting the cells with an oligodeoxynucleotide complementary to one or more regions of the HTLV-III genome and capable of hybridizing with said one or more regions of the HTLV-III genome, the regions being selected from the group consisting of:
  (a) the tRNA$^{lys}$ primer binding site;
  (b) regions of the HTLV-III genome vicinal in the 5' direction to the tRNA$^{lys}$ primer binding site;
  (c) the tRNA$^{lys}$ primer binding site of the HTLV-III genome and regions of the HTLV-III genome vicinal in the 5' direction to the tRNA$^{lys}$ primer binding site;
  (d) the mRNA donor splice sites of the HTLV-III genome;
  (e) the mRNA acceptor splice sites;
  (f) the initiator codon for the gag gene;
  (g) the initiator codon for the env gene;
  (h) the initiator codon for the tat gene;
  (i) the initiator codon for the sor gene;
  (j) the initiator codon fort the 3' orf gene;
  (k) the cap nucleotide of the HTLV-III genome;
  (l) the art gene or portions thereof;
  (m) the region of the HTLV-III genome encoding a frameshift; and
  (n) equivalents thereof, said equivalents being nucleotide sequences which are sufficiently similar in sequence to the complementary nucleotides to be capable of hybridizing with a conserved region of the HTLV-III genome and inhibiting its activity, under conditions appropriate for passage of said oligodeoxynucleotide into the cells in sufficient quantity to inhibit HTLV-III replication, HTLV-III gene expression or both.

5. A method of claim 4, in which the oligodeoxynucleotides are selected from the group consisting of:
  (a) CTGCTAGAGATddT;
  (b) CTGCTAGAGATTTTCCACAC;
  (c) TTCAAGTCCCTGTTCGGGCGCCAAA;
  (d) GCGTACTCACCAGTCGCCGC; and
  (e) CTGCTAGAGATTAA;
  (f) ACACCCAATTCTGAAAATGG; and
  (g) equivalents thereof.

6. A chemotherapeutic method of inhibiting HTLV-III replication, HTLV-III gene expression or both in an individual, comprising the oral or intravenous administration of an oligodeoxynucleotide complementary to one or more regions of the HTLV-III genome and capable of hybridizing with said one or more regions of the HTLV-III genome, said regions being selected from the group consisting of:
  (a) the tRNA$^{lys}$ primer binding site;
  (b) regions of the HTLV-III genome vicinal in the 5' direction to the tRNA$^{lys}$ primer binding site;
  (c) the tRNA$^{lys}$ primer binding site and regions of the HTLV-III genome vicinal in the 5' direction to the tRNA$^{lys}$ primer binding site;
  (d) the mRNA donor splice sites;
  (e) the mRNA acceptor splice sites;
  (f) the initiator codon for the gag gene;
  (g) the initiator codon for the env gene;
  (h) the initiator codon for the tat gene;
  (i) the initiator codon for the sor gene;
  (j) the initiator codon for the 3' orf gene;
  (k) the cap nucleotide;
  (l) the art gene or portions thereof;
  (m) the region of the HTLV-III genome encoding a frameshift; and
  (n) equivalents thereof, said equivalents being nucleotide sequences which are sufficiently similar in sequence to the complementary nucleotide sequences to be capable of hybridizing with a conserved region of the HTLV-III genome and inhibiting its activity.

7. A method of claim 6 in which the oligodeoxynucleotide is selected from the group consisting of:
(a) CTGCTAGAGATddT;
(b) CTGCTAGAGATTTTCCACAC;
(c) TTCAAGTCCCTGTTCGGGCGCCAAA;
(d) GCGTACTCACCAGTCGCCGC; and
(e) CTGCTAGAGATTAA;
(f) ACACCCAATTCTGAAAATGG;
(g) equivalents thereof.

8. A method of detecting the presence of HTLV-III virus in a sample by demonstrating inhibition of replication of said virus in cells which are normally killed by the HTLV-III virus after the cells have been (a) combined with said sample and an oligonucleotide complementary to at least one highly conserved region of the HTLV-III genome necessary for HTLV-III replication and capable of hybridizing with at least the highly conserved region, said highly conserved region of the HTLV-III genome being a nucleotide sequence present in the genomes of HTLV-III isolates and said oligonucleotide complementary to at least one highly conserved region of the HTLV-III genome necessary for HTLV-III replication being complementary to a region of the HTLV-III genome selected from the group consisting of:
(a) the tRNA$^{lys}$ primer binding site;
(b) regions of the HTLV-III genome vicinal in the 5' direction to the tRNA$^{lys}$ primer binding site;
(c) the tRNA$^{lys}$ primer binding site and regions of the HTLV-III genome vicinal in the 5' direction to the tRNA$^{lys}$ primer binding site;
(d) the mRNA donor splice sites;
(e) the mRNA acceptor splice sites;
(f) the initiator codon fot the gag gene;
(g) the initiator codon for the env gene;
(h) the initiator codon for the tat gene;
(i) the initiator codon for the sor gene;
(j) the initiator codon for the 3' orf gene;
(k) the cap nucleotide of the HTLV-III genome;
(l) the art gene or portions thereof;
(m) the region of the HTLV-III genome encoding a frameshift; and
(n) equivalents thereof, said equivalents being nucleotide sequences which are sufficiently similar in sequence to the complementary nucleotide sequences to be capable of hybridizing with a conserved region of the HTLV-III genome and inhibiting its activity and (b) maintained under conditions appropriate for cell growth.

9. A method of detecting the presence of HTLV-III virus in a liquid sample, comprising the steps of:
(a) combining an aliquot of the sample with cells which are normally killed by HTLV-III virus, to produce a control combination;
(b) combining a second aliquot of the sample with cells which are normally killed by the HTLV-III virus and an oligodeoxynucleotide complementary to at least one highly conserved region of the HTLV-III genome necessary for HTLV-III replication and capable of hybridizing with at least the highly conserved region, said highly conserved region of the HTLV-III genome being nucleotide sequences present in the genomes of HTLV-III isolates, to produce a test combination;
(c) maintaining said control combination and said test combination under conditions appropriate for cell growth; and
(d) comparing the growth of cells in said control combination with the growth of cells in said test combination in which the cells are normally killed by HTLV-III virus are T lymphocytes and the oligodeoxynucleotide complementary to at least one highly conserved region of the HTLV-III genome is complementary to at least one region of the HTLV-III genome selected from the group consisting of:
(a) the tRNA$^{lys}$ primer binding site;
(b) regions of the HTLV-III genome vicinal in the 5' direction to the tRNA$^{lys}$ primer binding site;
(c) the tRNA$^{lys}$ primer binding site of the HTLV-III genome and regions of the HTLV-III genome and regions of the HTLV-III genome vicinal in the 5' direction to the tRNA$^{lys}$ primer binding site;
(d) the mRNA donor splice sites of the HTLV-III genome;
(e) the mRNA acceptor splice sites:
(f) the initiator codon for the gag gene;
(g) the initiator codon for the env gene;
(h) the initiator codon for the tat gene;
(i) the initiator codon for the sor gene;
(j) the initiator codon for the 3' orf gene;
(k) the cap nucleotide of the HTLV-III genome;
(l) the art gene or portions thereof;
(m) the region of the HTLV-III genome encoding a frameshift; and
(n) equivalents thereof, said equivalents being nucleotide sequences which are sufficiently similar in sequence to the complementary nucleotide sequences to be capable of hybridizing with a conserved region of the HTLV-III genome and inhibiting its activity.

10. A method of detecting the presence of HTLV-III virus in a liquid sample, comprising the steps of:
(a) combining a first aliquot of the sample with transformed T lymphocyte cells, under conditions appropriate for cell growth;
(b) combining a second aliquot of the sample with transformed T lymphocyte cells and oligodeoxynucleotides complementary to at least one highly conserved region of the HTLV-III genome necessary for HTLV-III replication and capable of hybridizing with at least the highly conserved region, said highly conserved region of the HTLV-III genome being a nucleotide sequence present in the genomes of HTLV-III isolates, under conditions appropriate for cell growth;
(c) maintaining the combination formed in (a) and the combination formed in (b) under conditions appropriate for cell growth; and
(d) comparing visually the growth of cells in the combination formed in (a) with the growth of cells in the combination formed in (b),
the oligodeoxynucleotides complementary to at least one highly conserved region of the HTLV-III genome being complementary to a region of the HTLV-III genome selected from the group consisting of:
(a) the tRNA$^{lys}$ primer binding site;
(b) regions of the HTLV-III genome vicinal in the 5' direction to the tRNA$^{lys}$ primer binding site;
(c) the tRNA$^{lys}$ primer binding site and regions of the HTLV-III genome vicinal in the 5' direction to the tRNA$^{lys}$ primer binding site;
(d) the mRNA donor splice sites;
(e) the mRNA acceptor splice sites;
(f) the initiator codon for the gag gene;

(g) the initiator codon for the env gene;
(h) the initiator codon for the tat gene;
(i) the initiator codon for the sor gene;
(j) the initiator codon for the 3' orf gene;
(k) the cap nucleotide of the HTLV-III genome;
(l) the art gene or portions thereof;
(m) the region of the HTLV-III genome encoding a frameshift; and
(n) equivalents thereof, said equivalents being nucleotide sequences which are sufficiently similar in sequence to the complementary nucleotide sequences to be capable of hybridizing with a conserved region of the HTLV-III genome and inhibiting its activity.

11. A chemotherapeutic method of inhibiting HTLV-III replication, HTLV-III gene expression or both in peripheral human blood cells infected with HTLV-III or in T-lymphocyte cells infected with HTLV-III, comprising introducing into the cells oligodeoxynucleotides complementary to at least one highly conserved region of the HTLV-III genome necessary for HTLV-III replication, oligodeoxynucleotides complementary to at least one highly conserved region of the HTLV-III genome necessary for HTLV-III gene expression, alone or in combination, the complementary oligodeoxynucleotides selected from the group consisting of:
   (a) CTGCTAGAGATddt;
   (b) CTGCTAGAGATTTTCCACAC;
   (c) TTCAAGTCCCTGTTCGGGCGCCAAA;
   (d) GCGTACTCACCAGTCGCCGC;
   (e) CTGCTAGAGATTAA;
   (f) ACACCCAATTCTGAAAATGG; and
   (g) equivalents thereof, said equivalents being nucleotide sequences which are sufficiently similar in sequence to the complementary nucleotide sequences to be capable of hybridizing with a conserved region of the HTLV-III genome and inhibiting its activity, under conditions appropriate for entry of oligodeoxynucleotides into infected cells and binding to complementary regions of the HTLV-III genome.

12. A chemotherapeutic method of inhibiting HTLV-III replication, HTLV-III gene expression or both in peripheral human blood cells infected with HTLV-III or in T-lymphoctye cells infected with HTLV-III, comprising introducing into the cells oligodeoxynucleotides complementary to at least one highly conserved region of the HTLV-III genome and capable of hybridizing with at least the highly conserved region, the oligonucleotides being complementary to a region of the HTLV-III genome selected from the group consisting of:
   (a) the tRNA$^{lys}$ primer binding site;
   (b) regions of the HTLV-III genome vicinal in the 5' direction to the tRNA$^{lys}$ primer binding site;
   (c) the tRNA$^{lys}$ primer binding site and regions of the HTLV-III genome vicinal in the 5' direction to the tRNA$^{lys}$ primer binding site;
   (d) the mRNA donor splice sites;
   (e) the mRNA acceptor splice sites;
   (f) the initiator codon for the gag gene;
   (g) the initiator codon for the env gene;
   (h) the initiator codon for the tat gene;
   (i) the initiator codon for the sor gene;
   (j) the initiator codon for the 3' orf gene;
   (k) the cap nucleotide of the HTLV-III genome;
   (l) the art gene or portions thereof;
   (m) the region of the HTLV-III gene encoding a frameshift; and
   (n) equivalents thereof, said equivalents being nucleotide sequences which are sufficiently similar in sequence to the complementary nucleotide sequences to be capable of hybridizing with a conserved region of the HTLV-III genome and inhibiting its activity,
under conditions appropriate for entry of oligodeoxynucleotides into infected cells and binding to complementary regions of the HTLV-III genome.

* * * * *

UNITED STATES PATENT AND TRADEMARK OFFICE
CERTIFICATE OF CORRECTION

PATENT NO. : 4,806,463
DATED : February 21, 1989
INVENTOR(S) : John Goodchild and Paul C. Zamecnik It is certified that error appears in the above-indentified patent and that said Letters Patent is hereby corrected as shown below:

Column 1, line 4, insert -- This invention was made with government support under grant number R01-GM31562 and core grant P30 12708-15 from the National Institutes of Health. The government has certain rights in the invention.--

Signed and Sealed this

Thirteenth Day of September, 1994

Attest:

BRUCE LEHMAN

*Attesting Officer*     *Commissioner of Patents and Trademarks*